(12) United States Patent
Fang et al.

(10) Patent No.: US 7,312,301 B2
(45) Date of Patent: Dec. 25, 2007

(54) METHODS FOR THE FORMATION OF HYDROGELS USING THIOSULFONATE COMPOSITIONS AND USES THEREOF

(75) Inventors: Zhihao Fang, Madison, AL (US); Michael D. Bentley, Huntsville, AL (US)

(73) Assignee: Nektar Therapeutics AL, Corporation, Huntsville, AL (US)

( * ) Notice: Subject to any disclaimer, the term of this patent is extended or adjusted under 35 U.S.C. 154(b) by 540 days.

(21) Appl. No.: 10/751,010

(22) Filed: Dec. 31, 2003

(65) Prior Publication Data

US 2005/0143484 A1    Jun. 30, 2005

Related U.S. Application Data

(60) Provisional application No. 60/437,252, filed on Dec. 31, 2002.

(51) Int. Cl.
*C09K 5/06* (2006.01)
(52) U.S. Cl. ........................ 528/391; 523/122
(58) Field of Classification Search ............... 523/122; 528/391
See application file for complete search history.

(56) References Cited

U.S. PATENT DOCUMENTS

| | | | |
|---|---|---|---|
| 3,047,393 A | 7/1962 | Herz et al. | |
| 3,301,831 A | 1/1967 | Orthner et al. | |
| 3,812,071 A * | 5/1974 | Stoy | 524/796 |
| 4,273,667 A * | 6/1981 | Kent et al. | 252/70 |
| 4,609,438 A | 9/1986 | Torii et al. | |
| 4,894,238 A | 1/1990 | Embry et al. | |
| 4,960,689 A | 10/1990 | Nishikawa et al. | |
| 4,983,579 A | 1/1991 | Boden et al. | |
| 5,183,830 A | 2/1993 | Mohring et al. | |
| 5,393,798 A * | 2/1995 | Weber | 521/149 |
| 5,672,662 A | 9/1997 | Harris et al. | |
| 6,313,274 B1 | 11/2001 | Sykes et al. | |
| 6,512,098 B2 | 1/2003 | Jones et al. | |
| 6,646,083 B2 | 11/2003 | Hirano et al. | |
| 6,649,329 B2 | 11/2003 | Oya et al. | |
| 6,774,180 B2 * | 8/2004 | Kozlowski et al. | 525/54.1 |

FOREIGN PATENT DOCUMENTS

| | | |
|---|---|---|
| WO | WO 99/45964 | 9/1999 |
| WO | WO 01/26692 | 4/2001 |
| WO | WO 02/059179 | 8/2002 |

* cited by examiner

*Primary Examiner*—Randy Gulakowski
*Assistant Examiner*—John J. Figueroa
(74) *Attorney, Agent, or Firm*—Mark A. Wilson

(57) ABSTRACT

The present invention provides both crosslinked polymer compositions capable of forming hydrogel upon exposure to an aqueous environment and thiosulfonate hydrogel-forming components. The thiosulfonate hydrogel-forming components of the invention are preferably multi-arm thiosulfonate polymer derivatives that form a crosslinked polymer composition when exposed to a base without requiring the presence of a second cross-linking reagent, redox catalyst, or radiation. Methods for forming hydrogel compositions, as well as methods for using the hydrogel, are also provided.

12 Claims, No Drawings

METHODS FOR THE FORMATION OF HYDROGELS USING THIOSULFONATE COMPOSITIONS AND USES THEREOF

CROSS REFERENCE TO RELATED APPLICATION

This application claims the benefit of priority to U.S. Provisional Patent Application Ser. No. 60/437,252, filed Dec. 31, 2002, which is incorporated herein by reference.

FIELD OF THE INVENTION

The present invention relates generally to the field of polymer chemistry, and more particularly to the formation of hydrogel using thiosulfonate derivatives of water-soluble polymers.

BACKGROUND OF THE INVENTION

The hydrophilic polymer poly(ethylene glycol), abbreviated "PEG," also known as poly(ethylene oxide) abbreviated "PEO," poly(oxyethylene) abbreviated "POE," and poly(oxirane), is of considerable utility in biological applications and medicine. In its most common form, PEG is a linear polymer terminated at each end with hydroxyl groups:

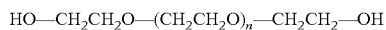

wherein (n') represents the number of repeating ethylene oxide monomers.

The above polymer, $\alpha$-,$\omega$-dihydroxylpoly(ethylene glycol), can be represented in brief form as HO-PEG-OH where it is understood that the -PEG- symbol represents the following structural unit:

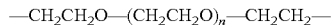

where (n') typically ranges from about 3 to about 4000.

A common form of PEG is methoxy-PEG-OH, or MPEG in brief, in which one terminus is the relatively inert methoxy group, while the other terminus is a hydroxyl group that is subject to ready chemical modification. The structure of MPEG is given below:

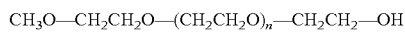

wherein (n') typically ranges from about 3 to about 4000.

Random or block copolymers of ethylene oxide and propylene oxide, shown below, are closely related to PEG in their chemistry, and they can be substituted for PEG in many of its applications.

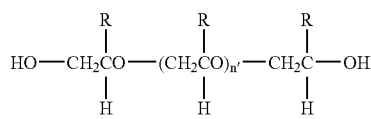

wherein each R is independently H or $CH_3$ and (n') typically ranges from about 3 to about 4000.

PEG is a polymer that is not only water soluble, but also is nontoxic and nonimmunogenic. Because of these properties, PEG has been covalently attached to insoluble molecules wherein the resulting PEG-molecule conjugate is soluble. For example, it has been shown that the water-insoluble drug paclitaxel, when coupled to PEG, becomes water soluble. Greenwald et al. (1995) *J. Org. Chem.* 60: 331-6.

PEG has also been used to form crosslinked matrices or gels. While such PEG-formed matrices and gels are often substantially nonsoluble, they are swellable in water. PEG hydrogel, which are water-swollen gels, have been used for wound covering and drug delivery. PEG hydrogel are prepared by incorporating PEG into a chemically crosslinked network or matrix so that the addition of water produces an insoluble, swollen gel. One application of such hydrogel involves the delivery of drugs wherein the drug molecules are entrapped within the crosslinked matrix. Delivery of the drug is effected as drug molecules pass through the interstices associated within the matrix and ultimately leave the matrix.

One approach for preparing PEG hydrogel is described in U.S. Pat. No. 4,894,238, in which hydrolytically stable and nondegradable urethane (also referred to as carbamate) linkages are described as providing a means to connect the termini of linear polymers. For example, a crosslinked network having urethane linkages is described as being prepared by combining PEG with a triol and a diisocyanate.

Another approach for preparing nondegradable PEG hydrogel is described in Gayet (1996) *J. Control. Release* 38: 177-84. In this approach, linear PEG is activated as the p-nitrophenylcarbonate and crosslinked by reaction with bovine serum albumin. Again, the linkages formed in this approach are hydrolytically stable urethane linkages.

U.S. Pat. No. 3,963,805 describes nondegradable PEG networks prepared by random entanglement of PEG chains. The described approach requires the use of PEG with acrylic acid and a free radical initiator such as acetyl peroxide.

U.S. Pat. No. 4,424,311 describes PEG hydrogel prepared by copolymerization of PEG methacrylate with other comonomers such as methyl methacrylate. This vinyl polymerization will produce a polyethylene backbone with PEG attached.

Sawhney et al. (1993) *Macromolecules* 26: 581 describes the preparation of block copolymers of polyglycolide or polylactide and PEG that are terminated with acrylate groups. Vinyl polymerization of the acrylate groups produces an insoluble, crosslinked gel with a polyethylene backbone. The ester groups associated with polylactide and polyglycolide segments within the polymer backbone are susceptible to slow hydrolytic breakdown, with the result that the crosslinked gel undergoes slow degradation and dissolution.

Other approaches for preparing nondegradable PEG hydrogel involve radiation-induced crosslinking of high molecular weight PEGs.

These prior art methods result in the incorporation of substantial nonPEG elements into the hydrogel composition including crosslinking agents and catalysts, and/or require the use of radiation as a crosslinking initiator. NonPEG elements, however, tend to introduce complexity into the hydrogel. Furthermore, the presence of nonPEG elements can result in toxic components being released in vivo upon the degradation and dissolution of the matrix. Further, harsh gelling conditions can inactivate or degrade drug substances that are often incorporated within a hydrogel composition.

As such, it would be desirable to provide improved hydrogel compositions and methods for forming such hydrogel compositions that are suited for biological applications. The present invention addresses these and other needs in the art by providing, inter alia, hydrogel lacking undesirable components as well as methods for forming hydrogel that do not require harsh conditions.

SUMMARY OF THE INVENTION

It is an object of the invention to provide crosslinked polymer compositions capable of forming hydrogel upon exposure to an aqueous environment and hydrogel-forming components. The hydrogel-forming components of the invention are preferably multi-arm thiosulfonate polymer derivatives. It has been unexpectedly found that multi-arm thiosulfonate polymer derivatives form a crosslinked polymer composition when exposed to a base and without requiring the presence of a second cross-linking reagent, redox catalyst, or radiation. In one embodiment, such multi-arm thiosulfonate polymer derivatives can also form a hydrogel by reaction with polymer derivatives having at least two thiol groups.

In one aspect of the invention, compositions are provided comprising a hydrogel-forming component of Formula (I):

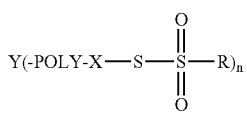

Formula (I)

wherein:

Y is a moiety derived from a molecule having at least three nucleophilic groups;

POLY is a water-soluble polymer;

(n) is an integer from 3 to about 100;

X is a linking group; and

R is an organic radical such as an alkyl or aryl group.

Optionally, the hydrogel-forming component of Formula (I) can contain at least one degradable linkage. A nonlimiting list of degradable linkages include those selected from the group consisting of amides, esters, carbonates, acetals, orthoesters, phosphates, and thiolesters. Advantageously, the presence of one or more degradable linkages in the hydrogel-forming component allows for the degradation of the polymer chains (e.g., by hydrolysis or enzymatic degradation) of the corresponding hydrogel. In this way, the breakdown and dissolution of the hydrogel can be effected following in vivo administration.

The invention further provides compositions comprising a hydrogel-forming component of Formula (II):

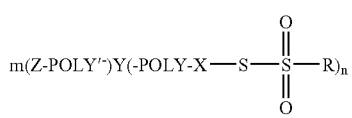

Formula (II)

wherein each of Y, POLY, X, R, and (n) are as defined above with respect to Formula (I), and further wherein POLY' is a water-soluble polymer (either the same or different than POLY), Z is a functional group having low reactivity (preferably no reactivity) with thiosulfonate, sulfhydryl (i.e., —SH), and disulfide linkages (i.e., —S—S— linkages), and (m) is a positive integer. Thus, the value of (m) can satisfy one or more of the following ranges: 1 or more, 2 or more, 3 or more, 5 or more, 10 or more, 15 or more, 50 or more, 75 or more, and 100 or more.

As previously indicated, POLY' can be the same or different than POLY. POLY' (like POLY) optionally includes a degradable linkage. With respect to the functional group "Z," nonlimiting exemplary functional groups from which Z may be selected include: active carbonate, acetal, acetamide, acrylol, aldehyde, aldehyde hydrates, alkenyl, acrylate, methacrylate, acrylamide, active sulfone, amine, carboxylic acid, epoxide, hydrazide, hydroxyl, glycol, glyoxals, guanido, isocyanate, isothiocyanate, keto, orthopyridyl-disulfide, dithiopyridine, vinylsulfone, vinylpyridine, diones, mesylates, tosylates, thiosulfonate, and tresylate and the like, as well as protected forms of any of the foregoing. Z may also include: N-succinimidyl, succinimidyl propionate, succinimidyl succinate, succinimidyl, glycidyl ether, oxycarbonylimidazole, and p-nitrophenylcarbonate.

Yet another embodiment of the invention employs molecules of Formula (III):

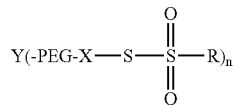

Formula (III)

wherein Y, X, R, and (n) are as defined above with respect to Formula (I), and PEG is a high or low molecular weight poly(ethylene glycol) moiety, optionally containing a degradable linkage.

In yet another aspect of the invention, hydrogel are provided. The hydrogel comprise polymers crosslinked to each other using disulfide bonds. The hydrogel can be prepared by linking one or more of the hydrogel-forming components encompassed by any of Formulas I-III. Typically, the linking of each hydrogel-forming component is carried out by treating a composition of hydrogel-forming components with a base. Preferably, the hydrogel is formed from hydrogel-forming components encompassed by Formula III, wherein (n) is 4. It is believed that such hydrogel-forming components are especially useful in the formation of hydrogel compatible with a variety of applications including biological applications.

It was unexpectedly discovered that the presently described hydrogel do not require the addition of a separate cross-linking agent or radiation (e.g., UV or microwave light) to result in their formation. Stated, differently, it was discovered that neither a separate cross-linking agent nor radiation was required to initiate the crosslinking reaction required to form a hydrogel with the hydrogel-forming components provided herein. As such, hydrogel of the invention can be formed from single component systems that are capable of in situ gelling upon exposure to base.

In addition to being suitable for hydrogel formation in situ, the hydrogel of the invention can be molded in a variety of shapes for use as scaffolds in biological applications and tissue engineering. The molded hydrogel are comprised of multiple layers or regions comprising different hydrogel compositions.

Another aspect of the invention provides for hydrogel formed from hydrogel-forming components of Formulas I-III that have been further stabilized by crosslinking with homofunctional or heterofunctional crosslinking agents. Crosslinking can also be accomplished by incorporating a naturally occurring or synthetic polymer bearing two or more groups capable of reacting with thiosulfonate groups, thiols or disulfides to form covalent linkages.

Yet another aspect of the invention provides for hydrogel-forming components and hydrogel associated with at least one biologically active moiety. Association of biologically active moieties can be through covalent attachment, either directly to the hydrogel-forming component or through the use of agents that couple the biologically active moiety to the hydrogel-forming component. Alternatively or in addition, biologically active moieties can be entrapped within the hydrogel using noncovalent interactions such as ionic interactions.

In yet another aspect of the invention, hydrogel-forming component and hydrogel associated with at least one active agent can also be used for localized delivery of the active agent. For example, active agents can be delivered from the hydrogel to a local tissue site, thereby facilitating tissue healing and regeneration.

DETAILED DESCRIPTION OF THE INVENTION

The present invention will now be described more fully. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

It must be noted that, as used in this specification and the claims, the singular forms "a," "an," and "the" include plural referents unless the context clearly dictates otherwise. Thus, for example, reference to "a drug" includes a single drug as well as two or more of the same or different drugs, reference to a "hydrogel-forming component" includes a single hydrogel-forming component as well as two or more of the same of different hydrogel-forming components, and the like.

The terms "functional group," "active moiety," "activating group," "reactive site," "endgroup," "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react (i.e., "nonreactive" or "inert" groups). For example, as would be understood in the art, the term "active ester" includes those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group. As used herein, the term "functional group" includes protected functional groups.

The term "protected functional group" refers to the presence of a protecting group or moiety that prevents reaction of the chemically reactive functional group under certain reaction conditions. The protecting group will vary depending on the type of chemically reactive group being protected and the reaction conditions employed. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention, see for example, Greene, T. W., et al., *PROTECTIVE GROUPS IN ORGANIC SYNTHESIS*, 3rd ed., John Wiley & Sons, New York, N.Y. (1999).

An "organic radical," in the context describing a structure, a structural formula, a molecule, and so forth, refers to a carbon-containing moiety wherein a carbon atom provides a point of attachment. Exemplary organic radicals include, alkyl (e.g., lower alkyl), substituted alkyl (including heteroalkyl, and chain-substituted heteroalkyl), alkenyl, substituted alkenyl, alkynyl, substituted alkynyl, aryl, substituted aryl, heteroaryl, substituted heteroaryl, heterocyclicyl, substituted heterocyclicyl, and so forth.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, etc.).

As used herein, "alkenyl" refers to a branched or unbranched hydrocarbon group of 2 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to branched or unbranched hydrocarbon group of 2 to 15 atoms in length, containing at least one triple bond, and includes, for example, ethynyl, propynyl, butynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, and nitrogen, or a combination thereof. Heteroaryl rings may also be fused with one or more cyclic hydrocarbon, heterocyclic, aryl, or heteroaryl rings.

"Heterocyclicyl" or "heterocyclic" means a group of one or more rings of 5-12 atoms, preferably 5-7 atoms, with or without unsaturation or aromatic character and having at least one ring atom which is not a carbon. Preferred heteroatoms include sulfur, oxygen, and nitrogen.

The term "substituted" as in, for example, "substituted alkyl," refers to a moiety (e.g., an alkyl group) substituted with one or more non-interfering substituents, such as, but not limited to: $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Substituted heteroaryl" is heteroaryl having one or more noninterfering groups as substituents.

"Substituted heterocyclicyl" is a heterocyclicyl group having one or more side chains formed from noninterfering substituents.

"Noninterfering substituents" are those groups that, when present in a molecule, are typically nonreactive with other functional groups contained within the molecule.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

As used herein, "nonpeptidic" refers to a structure substantially free of amino acids connected via peptide linkages. Thus, for example, when nonpeptidic is used in reference to a polymer backbone, the polymer backbone is substantially free of amino acids connected via peptide linkages. The polymer backbone may, however, include a minor number of peptide linkages spaced along the length of the backbone, such as, for example, no more than about 1 peptide linkage per about 50 monomer units.

A "polymer conjugate" refers to a water-soluble polymer covalently attached to a biologically active moiety, as defined herein. In the case that a polymer conjugate is reacted with a second polymer so as to form an extended polymer backbone, whether or not the joinder of the polymers is with a peptidic or other linkage, the term "polymer conjugate" refers to the overall length of polymer bound to the biologically active agent.

The term "linkage" or "linker" is used herein to refer to an atom, groups of atoms, or bonds that are normally formed as the result of a chemical reaction. A linker of the invention typically links adjacent moieties, such as two polymer segments, via one or more covalent bonds. Hydrolytically stable linkages are linkages that are substantially stable in water and do not react to any significant degree with water at useful pHs, e.g., under physiological conditions, for an extended period of time, perhaps even indefinitely. A hydrolytically unstable or degradable linkages means a linkage that is degradable in water or in aqueous solutions, including for example, blood, plasma or other physiological fluid. Enzymatically unstable or degradable linkages encompass those linkages can be degraded by one or more enzymes.

The terms "drug," "biologically active molecule," "biologically active moiety," "biologically active agent," "active agent," and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs (e.g., nonpeptidic drugs), dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The terms "low weight polymer" and "low molecular weight polymer" broadly refer to a linear, branched, multi-arm, or forked polymer backbones comprising a water-soluble and nonpeptidic polymer having from 1 to about 120 repeating units. These polymers typically have from 1 to 2 functional groups, typically located at opposite ter mini on a linear polymer, to about 300, which can be located at the termini of highly branched or multiarmed structures, although a smaller number may be located along the polymer backbone. Although the molecular weight of the small polymer or oligomer can vary, it is typically in the range of from about 100 Da to about 10,000 Da, depending, of course, on the molecular weight of the individual repeating units. In the case of PEG, one PEG monomer unit has a molecular weight of about 44 Da and low weight polymers will have a molecular weight of from about 44 Da to about 5280 Da. Molecular weights of 2000, 3200, 3400, and 5,000 are available commercially.

The terms "high weight polymer" and "high molecular weight polymer" broadly refer to a linear, branched, or multi-arm polymer backbone comprising a water-soluble and nonpeptidic polymer having more than about 200 repeating units. These polymers typically have from 1 to 2 functional groups, typically located at opposite termini on a linear polymer, to about 300, which can be located along the polymer backbone or at the termini of highly branched or multiarmed structures. Forked structures are also contemplated in which a terminus is branched to provide two functionalities. In the case of PEG, high weight polymers have a molecular weight above about 8,800 Da. Commercially available PEGs include those having a nominal molecular weight of 10,000 Da, 12,000 Da, 15,000 Da, 18,000 Da, 20,000 Da, 30,000 Da, 40,000 Da, and above. Straight and branched PEGs are readily available at higher molecular weights.

Reference to a "molecular weight" in the context of a water-soluble polymer refers to the mass average molecular weight of the polymer, typically determined by size exclusion chromatography, light scattering techniques, or intrinsic velocity determination in 1,2,4-trichlorobenzene.

As used herein, "PEG" broadly refers to a linear, multi-arm, or branched polymer backbone comprising a water-soluble and non-peptidic polymer having repeat $CH_2CH_2O$ units. The polymer $\alpha,\omega$-dihydroxypoly(ethylene glycol), can be represented in brief form as HO-PEG-OH where it is understood that the -PEG- symbol represents the following structural unit —$CH_2CH_2O$—$(CH_2CH_2O)_n$—$CH_2CH_2$— where (n') typically ranges from about 3 to about 4000. The PEG family of polymers generally exhibits the properties of solubility in water and in many organic solvents, lack of toxicity, and lack of immunogenicity. The term PEG should be understood to be inclusive and to include poly(ethylene glycol) in any of its linear, branched or multi-arm forms, including alkoxy PEG, bifunctional PEG, forked PEG, branched PEG, pendant PEG, and PEG with degradable linkages therein.

PEG, in any of the forms described herein, is typically clear, colorless, odorless, soluble in water, stable to heat, inert to many chemical agents, does not hydrolyze or deteriorate (unless specifically designed to do so), and is generally nontoxic. Poly(ethylene glycol) is considered to be biocompatible, which is to say that PEG is capable of coexistence with living tissues or organisms without causing harm. More specifically, PEG is substantially nonimmunogenic, which is to say that PEG does not tend to produce an immune response in a patient. When attached to a molecule having some desirable function in the body, such as a biologically active agent, the PEG tends to mask the agent and can reduce or eliminate any immune response so that an organism can tolerate the presence of the agent. PEG-containing conjugates and hydrogel tend not to produce a substantial immune response or cause clotting or other undesirable effects.

As used herein, "hydrogel" are compositions resulting from the association of one or more types of molecules to form a substantially nonwater soluble material. "Hydrogel" is not meant to indicate that the material is rigid, but rather that the composition has undergone linking such that the components of the hydrogel substantially interact. Hydrogel of this invention will span the range of viscosity from solutions, some of which appear viscous in nature, through gels, which substantially retain their shape and structure when unsupported.

The term "patient," refers to a living organism suffering from or prone to a condition that can be prevented or treated by administration of a drug, and includes both humans and animals.

"Optional" or "optionally" means that the subsequently described circumstance may or may not occur, so that the description includes instances where the circumstance occurs and instances where it does not.

II. Thiosulfonate Polymer Derivatives

In a first aspect of the invention, thiosulfonate polymer derivatives are provided which are capable of crosslinking upon exposure to basic conditions. Preferably, the thiosulfonate polymer derivatives of the invention are multi-arm thiosulfonates of water-soluble polymers. In a preferred embodiment of the invention, hydrogel-forming components are provided comprising molecules encompassed by Formula (I):

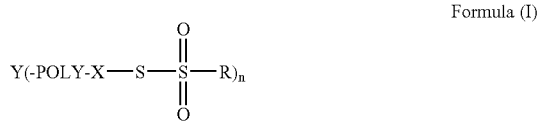

Formula (I)

wherein:
Y is a moiety derived from a molecule having at least three nucleophilic groups;
POLY is a water-soluble polymer;
(n) is an integer from 3 to about 100;
X is a linking group; and
R is an organic radical such as an alkyl or aryl group.

The water-soluble polymer (such as POLY and POLY') useful in this invention include any water-soluble polymers and the invention is not limited in this regard. The water-soluble polymer can include polyamides such as polypeptides. In addition, water-soluble polymers that are nonpeptidic are particularly useful in the invention. By way of example, a water-soluble polymer as used herein can be poly(alkylene glycol), including poly(ethylene glycol) (PEG), poly(propylene glycol) (PPG) or copolymers of poly(alkylene) glycols including copolymers of poly(ethylene glycol) and poly(propylene glycol), poly(lactide), poly(glycolide), poly(caprolactone), poly(oxyethylated polyol), poly(olefinic alcohol), poly(vinylpyrrolidone), N-(2-hydroxypropyl) methacrylamide, poly-1,3-dioxolane, poly-1,3,6-trioxolane, poly(hydroxypropylmethacrylamide), poly(hydroxyalkylmethacrylamide), poly(hydroxyalkylmethacrylate), poly(α-hydroxy acid), poly(vinyl alcohol), polyphosphazene, polyoxazoline, poly(saccharides), carboxymethylcellulose, dextran, copolymers of ethylene/maleic anhydride copolymers, polylactide/polyglycolide copolymers, propylene oxide/ethylene oxide copolymers, copolymers of polyethylene glycol and an and amino acid, and poly(N-acryloylmorpholine), such as described in U.S. Pat. No. 5,629,384, which is incorporated by reference herein in its entirety. The preferred polymer is poly(ethylene glycol) having a size from about 200 Da to about 20,000 Da, or more preferably from about 500 Da to about 15,000 Da or more preferably from about 600 Da to about 6000 Da.

Those of ordinary skill in the art will recognize that the foregoing list for substantially water soluble polymers is by no means exhaustive and is merely illustrative, and that all polymeric materials having the qualities described above are contemplated.

The linking group serves to link the thiosulfonate to the water-soluble polymer. Preferred linking groups are selected from the group consisting of alkylene groups, alkylene amides, alkylene esters, or alkylene ethers. Specific examples of a suitable linking group include those selected from the group consisting of —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—

—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)— —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—. The linking group can be joined to the water-soluble polymer by a variety of linkages, including but not limited to: ether, thioether, amine, amide, ester or single, double or triple carbon-carbon bonds.

Y can be any moiety derived from a molecule having 3 or more nucleophilic groups. Preferably, the "Y" moiety has a branching core structure providing from 3 to about 100 available groups for the attachment of POLY, and typically provides about 3 to 20, 4 to 25, or 5 to 30 available groups, such that the branched polymer structure has from 3 to about 100 polymer chains, although there may be more groups present on Y than polymer chains attached thereto. Preferred available groups for the attachment of polymers to Y include hydroxyl and amino groups. Y moieties can be derived from glycerol, oligoglycerols, pentaerythritol, carbohydrates, cyclodextrin, or amine analogues of these molecules (e.g., Y may be a substituted glycerol or 1,2,3-propane-triamine).

The value of (n) is preferably at least 3, 4, 5, 6, 10, 15, 25, 50, 75, or 100. The value of (n) depends on the nature of the Y moiety employed. Typically, however the value of (n) will satisfy one or more of the following ranges: 3-4; 3-5; 3-10; 4-5; 4-6; 4-10; 5-6; 5-10; 5-25; 10-25; 25-50; 50-75; and 75-100.

Optionally, the water-soluble polymer can include at least one degradable linkage. Preferred degradable linkages are selected from the group consisting of amides, imines, esters, carbonates, hydrazone, acetals, orthoesters, phosphates, and thiolesters. These and other degradable linkages allow for the degradation of the water-soluble polymers associated therein. Degradation of water-soluble polymers, in turn, can result in the breakdown and dissolution of any hydrogel formed by degradable linkage-containing water-soluble polymers and derivatives thereof. Such linkages are typically subject to degradation by hydrolysis or enzymatic degradation.

The formation of such linkages is known to those of ordinary skill in the art and can be accomplished by reacting two water-soluble polymers, each bearing a different reactive group such that the bond resulting from the two different reactive groups is a degradable linkage. Briefly, exemplary linkages can be formed as followed: imine linkages result, for example, from reaction of an amine and an aldehyde (see, e.g., Ouchi et al. (1997) *Polymer Preprints* 38(1): 582-3, which is incorporated herein by reference.); phosphate ester linkages are formed, for example, by reacting an alcohol with a phosphate group; hydrazone linkages result, for example, by reaction of a hydrazide and an aldehyde; acetal linkages are formed by, for example, reaction between an aldehyde and an alcohol; orthoester linkages are formed by, for example, reaction between a formate and an alcohol. Water-soluble polymers bearing these and other reactive groups are commercially available or can be synthesized by one having ordinary skill in the art.

In addition to the incorporation of degradable linkages into the water-soluble polymer, the degradable linkages of the backbone can be employed to covalently attach biologically active moieties to the polymer backbones through a weak or degradable linkage moiety. Such linkage moieties generally degrade under physiological conditions, typically by hydrolysis or enzymatic cleavage, resulting in the release of the biologically active moieties from the polymer backbone.

The invention also provides molecules encompassed by Formula (II). Essentially, the molecules of Formula (II) comprise the additional moiety -POLY'-Z attached to the Y moiety of Formula (I). Thus, the molecules of Formula (II) comprise the following structure:

Formula (II)

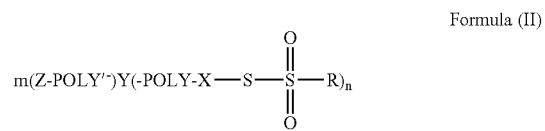

wherein each of Y, POLY, X, R, and (n) are as defined above with respect to Formula (I), and further wherein POLY' is a water-soluble polymer (either the same or different than POLY), Z is a functional group having low reactivity (preferably no reactivity) with thiosulfonate, sulfhydryl (i.e., —SH), and disulfide linkages (i.e., —S—S— linkages), and (m) is a positive integer.

The value of (m) is 1 or more, 2 or more, 3 or more, 5 or more, 10 or more, 15 or more, 25 or more, 50 or more, 75 or more, or 100 or more. In this embodiment, POLY' may be the same or different than POLY. Both POLY and POLY' are selected from the group defined for POLY in formula (I) above and may include a degradable linkage.

Z can be any functional group with a desired functionality, as would be recognized by one skilled in the art. In one embodiment, Z may be a functional group which is of low reactivity or nonreactive with thiosulfonate, —SH, or —S—S— linkages. In addition, Z can be a group capable of reacting with an active agent, thereby providing a hydrogel-forming component—as well as a hydrogel formed therefrom—containing a covalently bond active agent. Exemplary functional groups in this regard include hydroxyl, active ester (e.g. N-hydroxysuccinimidyl ester or 1-benzotriazolyl ester), active carbonate (e.g. N-hydroxysuccinimidyl carbonate and 1-benzotriazolyl carbonate), acetal, aldehyde, aldehyde hydrate, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, or tresylate.

Specific examples of "Z" functional groups for covalent attached to an active agent include N-succinimidyl carbonate (see e.g., U.S. Pat. Nos. 5,281,698, and 5,468,478), amine (see, e.g., Buckmann et al. (1981) *Makromol. Chem.* 182: 1379, and Zalipsky et al. (1983) *Eur. Polym. J.* 19: 1177), hydrazide (See, e.g., Andresz et al. (1978) *Makromol. Chem.* 179: 301), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997, and U.S. Pat. No. 5,672,662), succinimidyl succinate (see, e.g., Abuchowski et al. (1984) *Cancer Biochem. Biophys.* 7: 175, and Joppich et al. (1979) *Makromol. Chem.* 180: 1381), succinimidyl ester (see, e.g., U.S. Pat. No. 4,670,417), benzotriazole carbonate (see, e.g., U.S. Pat. No. 5,650,234), glycidyl ether (see, e.g., Pitha et al. (1979) *Eur. J. Biochem.* 94: 11, and Elling et al. (1991) *Biotech. Appl. Biochem*. 13: 354), oxycarbonylimidazole (see, e.g., Beauchamp et al. (1983) *Anal. Biochem*. 131: 25, and Tondelli et al. (1985) *J. Controlled Release* 1: 251), p-nitrophenylcarbonate (see, e.g., Veronese, et al. (1985) *Appl. Biochem. Biotech*. 11: 141, and Sartore et al. (1991) *Appl. Biochem. Biotech*. 27: 45), aldehyde (see, e.g., Harris et al. (1984) *J. Polym. Sci. Chem. Ed*. 22: 341, and U.S. Pat. Nos. 5,824,784, and 5,252,714), maleimide (see, e.g., Goodson et al. (1990) *Bio/Technology* 8: 343, Romani et al. (1984) *Chemistry of Peptides and Proteins* 2: 29), and Kogan (1992) *Synthetic Comm*. 22: 2417), orthopyridyl-disulfide (see, e.g., Woghiren et al. (1993) *Bioconj. Chem*. 4: 314), acrylol (see, e.g., Sawhney et al. (1993) *Macromolecules* 26: 581), and vinylsulfone (see, e.g., U.S. Pat. No. 5,900,461). All of the above references are incorporated herein by reference.

Inclusion of —POLY'—Z moieties permits a change in the characteristics of the resultant hydrogel compositions. For example, when Z is amine, the resultant hydrogel will be cationically charged at neutral pH, and as such may form associations with negatively charged active agents such as typical nonsteroidal anti-inflammatory drugs ("NSAIDs"), or polyanionic materials such as condroitin sulfate, either of which maybe incorporated into the hydrogel when it is formed or after it has been prepared. In addition, it is possible to form covalent attachments to Z groups such as amines either directly, or through the use of amine-reactive crosslinking agents.

Yet another embodiment of the invention employs molecules of Formula (II):

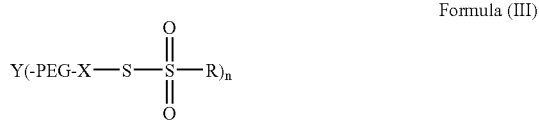

Formula (III)

wherein Y, X, R, and (n) are as defined above with respect to Formula (I), and PEG is a high or low molecular weight poly(ethylene glycol) moiety, optionally containing a degradable linkage.

A preferred embodiment of the invention employs molecules of Formula (III), wherein (n) is 3, 4, or 8. Such 3-, 4-, and 8-arm PEG molecules are especially useful in the formation of hydrogel compatible with a variety of applications including biological applications.

Without intending to be limited by theory, it is believed that the thiosulfonate polymer derivatives of the invention release a sulfonate leaving group upon exposure to a base, thereby generating a reactive thiol group in situ. This thiol group is then available for reaction with appropriate electrophilic functional groups such as a thiosulfonate group associated with the thiosulfonate-containing hydrogel-forming components described herein.

III. Hydrogel Compositions

Another aspect of the invention is directed to crosslinked polymer compositions capable of forming a hydrogel composition upon exposure to an aqueous environment. The hydrogel compositions are characterized as having a relatively low gel time with a viscosity suited for administration to a patient. The hydrogel compositions of the invention can be formed from the hydrogel-forming components previously described. Thus, the hydrogel-forming components are preferably thiosulfonate polymer derivatives, and more preferably multi-arm thiosulfonate esters of a water-soluble polymer such as those encompassed by Formulas I-III. In a preferred embodiment, hydrogel compositions of the invention are formed from a composition comprising only one type of hydrogel-forming component. Such a "single-component" system is advantageously less costly to make, easier to store and package, and relatively simple to form into a hydrogel composition. The single-component composition comprises a thiosulfonate polymer derivative. Moreover, the hydrogel composition preferably lacks by-products of crosslinking agents. In addition, the hydrogel composition preferably lacks redox catalysts.

As used herein, a single component hydrogel-forming composition generally refers to a composition comprising only a single component that is involved in crosslinking to form the hydrogel composition. As such, a single component hydrogel-forming composition can comprise additional components such as buffers and biologically active moieties, but will generally only include a single hydrogel-forming component capable of crosslinking. In some embodiments, however, the hydrogel may be subsequently modified by the incorporation of additional components such as biologically active moieties or stabilizing crosslinking agents. Modification of hydrogel to incorporate additional components may be accomplished either by covalent or noncovalent association with the hydrogel.

Noncovalent association of additional components with the hydrogel of this invention may be accomplished by entrapment of the components within the hydrogel during its formation. Alternatively, additional components may be associated with the hydrogel of this invention by contacting the component with the formed hydrogel. Noncovalent association of active agents that are entrapped or contacted with the hydrogel of this invention may further include the formation of complexes resulting from ionic interactions. In some embodiments of this invention, such ionic interactions can be effected by the incorporation of free amino groups into the molecules of Formula (II) where Z is an amino group. In yet other embodiments of this invention, ionic interactions are effected by incorporating carboxyl groups into the molecules of Formula (II) where Z is a carboxyl group.

Covalent attachment of additional components to the hydrogel compositions of the invention can be accomplished by modification of the thiosulfonate hydrogel-forming components prior to hydrogel formation, concurrent with hydrogel formation, or by modification of a hydrogel once it has been formed. Such covalent attachment can be achieved through direct covalent linkage of the molecules to the hydrogel or hydrogel-forming component. By way of example, direct covalent linkage is possible where the additional component bears a pendant reactive group that can form a linkage with thiosulfonate, thiol or disulfide groups present in the hydrogel-forming component or the formed hydrogel. Alternatively, additional components may be covalently attached to the hydrogel or hydrogel-forming component by the interposition of a crosslinking agent between the polymer and the additional component. Crosslinking agents useful for this purpose include homobifunctional, heterobifunctional, and trifunctional crosslinking agents.

Without intending to be limited by theory, the hydrogel compositions of the invention will generally comprise disulfide bonds formed between thiosulfonate functional groups of the hydrogel-forming components and thiol groups that are generated in situ upon exposure of the hydrogel-forming components to base. Such disulfide bonds are generally not biodegradable unless internalized by a cell or exposed to disulfide reduction agents such as reduced gluthathione. However, hydrolytically or enzymatically unstable linkages can be incorporated into the polymer backbone of the hydrogel-forming components to allow for biodegradable hydrogel compositions.

As discussed above, hydrogel compositions of the invention can therefore be formed from single component hydrogel-forming compositions without the need for a second reagent such as a crosslinking agent or redox catalyst. The hydrogel composition can additionally contain leaving groups such as methane sulfonate and methane sulfinate, but is preferably lacking crosslinking groups. Since the mixture can be formed from a single component composition, the end user does not have to adjust the proportion of hydrogel-forming components. This, in turn, leads to greater uniformity in the resulting hydrogel and ease of use. Further, the base crosslinking initiator is easily neutralized in vivo, thereby improving the biocompatibility of the hydrogel.

In a preferred embodiment, the hydrogel compositions of the invention may optionally be associated with at least one active agent, either through a covalent attachment or through a noncovalent attachment. Such active agents can be noncovalently associated with the hydrogel compositions of the invention by adding them to the hydrogel-forming components prior to the formation of the hydrogel, thereby entrapping them within the gel upon its formation. Active agents can also be noncovalently associated with the hydrogel of this invention by contacting the formed hydrogel with the active agent for a period of time sufficient to permit incorporation within the hydrogel (e.g., a period of from several minutes to several hours or days).

In addition, an active agent can be incorporated into the hydrogel compositions of the invention by covalently binding the active agent directly or indirectly to the functional groups present on a hydrogel-forming component (e.g., the functional group "Z" included encompassed by a polymer of Formula II). As discussed above, the interaction of active agents with the hydrogel compositions may be modified through incorporation of one or more charged groups into the hydrogel forming components, or by incorporating charged components into the hydrogel compositions themselves. Further, association of active agents can be limited to outer surfaces or to regions accessible by diffusion, if desired.

Any active agent can be associated with the hydrogel and hydrogel-forming components and the invention is not limited in this regard. Suitable agents can be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, antibody fragments, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-571, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab, visilizumab, tacrine, memantine, rivastigmine, galantamine, donepezil, levetiracetam, repaglinide, atorvastatin, alefacept, vardenafil, sildenafil, and valacyclovir.

Additional agents suitable for covalent attachment include, but are not limited to, adefovir, alosetron, amifostine, amiodarone, aminocaproic acid, aminohippurate sodium, aminoglutethimide, aminolevulinic acid, aminosalicylic acid, amsacrine, anagrelide, anastrozole, aripiprazole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, dutasteride, epirubicin, estramustine, etoposide, exemestane, ezetimibe, fexofenadine, fludarabine, fludrocortisone, fluorouracil, fluoxymesterone, flutamide, fondaparinux, fulvestrant, gamma-hydroxybutyrate, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, nitisinone, octreotide, oxaliplatin, pamidronate, pentostatin, pilcamycin, porfimer, prednisone, procarbazine, prochlorperazine, ondansetron, palonosetron, oxaliplatin, raltitrexed, sirolimus, streptozocin, tacrolimus, pimecrolimus, tamoxifen, tegaserod, temozolomide, teniposide, testosterone, tetrahydrocannabinol, thalidomide, thioguanine, thiotepa, topotecan, treprostinil, tretinoin, valdecoxib, celecoxib, rofecoxib, valrubicin, vinblastine, vincristine, vindesine, vinorelbine, voriconazole, dolasetron, granisetron; formoterol, fluticasone, leuprolide, midazolam, alprazolam, amphotericin B, podophylotoxins, nucleoside antivirals, aroyl hydrazones, sumatriptan, eletriptan, macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, Factor IX, GCSF, GMCSF, hGH, insulin, FSH, and PTH.

Nucleic acids or polynucleotides which may be associated with the hydrogel compositions of the invention include naturally occurring nucleic acids, synthetic nucleic acids and nucleic acids prepared genetic engineering techniques. The nucleic acids may include genomic nucleic acids, such as the genomic DNA or RNA of viral vectors, or fragments of nucleic acids, such as genes or portions thereof including portions encoding proteins and capable of causing the expression of such proteins or fragments thereof when introduced into appropriate cells. The nucleic acids which may be associated with the hydrogel compositions of the invention may be in the form of one or more linear or circular constructs such as plasmids, cosmids, yeast artificial chromosomes, bacterial artificial chromosomes or they may be in the form of viral or bacterial vectors. Other nucleic acids which may be incorporated for delivery include ribozymes, antisense molecules and antisense expressing constructs.

Whether the active agent is incorporated into the hydrogel compositions by covalent or noncovalent associations, it is possible to modify their interactions with the hydrogel by the incorporation of one or more charged groups into the hydrogel forming components so that they form a charged hydrogel. Alternatively, it is possible to incorporate additional charged components, such as charged polymers into the hydrogel. Depending on the degree and nature of the charge this will effect both the capacity of the hydrogel to associate with the biologically active moiety and the kinetics of its release.

Synthetic polymers, naturally occurring polymers and polymers derived from naturally occurring polymers may also be incorporated into the hydrogel of this invention. Naturally occurring polymers and their derivatives that can be incorporated into the hydrogel compositions of the invention include polysaccharides and glycosaminoglycans, nucleic acids, proteins and peptides. Useful proteins include, but are not limited to, antibodies, monoclonal antibodies, chimeric antibodies, single chain antibodies, Fab fragments, enzymes, hormones, albumins, immunoglobins, peptide hormones, growth factors, and structural proteins such as collagen, fibrin, fibrinogen fibronectin, vitronectin, osteonectin, and laminin. When these polymers also contain functional groups that will react with the functional groups of the hydrogel-forming components, or the hydrogel formed therefrom, they will become linked to the hydrogel composition.

Hydrogel compositions of the invention may be prepared prior to use. Formed hydrogel compositions may optionally be subject to dehydration or lyophilization in order to remove bound water and used as either the intact hydrogel or reduced to powder or particulate form. Hydrogel compositions of the invention can also be employed without dehydration or lyophilization as formed objects or maybe incorporated into delivery systems including without limitation: ocular insert, suppositories, pessaries, transdermal patches, or capsules filled with the hydrogel compositions.

Regardless of the form of the hydrogel-forming composition or hydrogel composition, it is possible to package the compositions in single use, multiple use or bulk containers. The preparations can optionally be sterilized by art-recognized procedures. In one preferred embodiment, the materials are packaged in sterile, single-use containers. In other embodiments, the materials are packaged for ease of reconstitution by addition of water, aqueous solutions or suspensions in single or multiple use containers. In another embodiment, the materials are sold as a kit with a base to initiate gel formation. Optionally the kit can contain a premeasured amount of water stored in a separate container and/or directions for preparing the hydrogel.

IV. Hydrogel Formation and Reaction Conditions

In yet another aspect of the invention, methods for forming hydrogel compositions (i.e., crosslinked polymer compositions capable of forming a hydrogel upon exposure to an aqueous environment) from hydrogel-forming compositions are provided. Preferably, the hydrogel forming-compositions comprise thiosulfonate hydrogel-forming components, and more preferably thiosulfonate polymer derivatives. It has been unexpectedly discovered that hydrogel compositions can be formed from multi-arm thiosulfonate esters of water-soluble polymers without the addition of a second hydrogel-forming component, such as a crosslinking agent or redox catalyst, or radiation, such as UV or microwave. Due to these mild gelling conditions, the invention is compatible for use in variety of sensitive applications, including biological applications. Further, it was unexpectedly discovered that the physical properties of the hydrogel can be adjusted to desired parameters by controlling the gelling conditions.

In general, methods of the invention include providing a hydrogel-forming composition comprising at least one thiosulfonate polymer derivative, and exposing the composition to a basic pH under desired gelling conditions to thereby initiate crosslinking. The hydrogel-forming composition will preferably be substantially free of a second hydrogel-forming component such as a crosslinking agent or redox catalyst. Further, the thiosulfonate polymer derivative of the hydrogel-forming composition is preferably a multi-arm thiosulfonate ester of a water-soluble polymer, such as those of Formulas I-III described above. In one embodiment, the hydrogel-forming composition is preferably a single component hydrogel-forming composition as described above. Alternatively, the hydrogel-forming composition can comprise a mixture of different thiosulfonate polymer derivatives.

Again, without intending to be limited by theory, it is believed that the thiosulfonate polymer derivatives of the invention release a sulfonate leaving group upon exposure to a base, thereby generating a reactive thiol group in situ. This reactive thiol group is then available for reaction with appropriate electrophilic functional groups such as thiosulfonate groups. As such, upon exposure to a base, the thiosulfonate hydrogel polymer derivatives of the invention release a sulfonate leaving group to generate in situ a thiol group, which then forms a disulfide bond with remaining thiosulfonate groups of other thiosulfate polymer derivatives to thereby form a crosslinked hydrogel composition.

More particularly, it was found that the physical properties of a hydrogel formed according to the method of the invention can be controlled through the selection of desired gelling conditions such as pH, temperature, and polymer concentration. These gelling conditions can influence the gel time, viscosity, and degree of crosslinking within the hydrogel. As such, according to a preferred embodiment of the invention, a hydrogel with specific desired physical properties can be formed from a single component hydrogel-forming composition of thiosulfonate esters of water-soluble polymers without the need for a second hydrogel-forming component or exposure radiation. The hydrogel so formed can exhibit desired physical properties and be substantially free from by-products of a second hydrogel-forming component.

Preferred gelling conditions include any basic pH and/or temperature that does not cause undesired degradation of the hydrogel-forming composition. Such conditions can be determined experimentally. Preferred pH values range from about 7.4 to about 11, more preferably from about 7.4 to about 9.0, with a pH of about 8.0 being particularly preferred. Preferred temperatures range from about 20° C. to about 50° C., with temperatures ranging from about 25° C. to about 37° C. being particularly preferred. Preferred thiosulfonate polymer derivative concentrations are generally only limited by solubility, but preferably range from about 2% to about 25% wt/vol, and more preferably from about 2% to about 10% wt/vol, based on the total volume of hydrogel-forming composition under basic conditions. Although any base can be used to initiate the reactions required for crosslinking, exemplary bases suited for this purpose include sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The gelling conditions may be selected to obtain a desired gel time, hydrogel viscosity, and degree of crosslinking, as recognized by one skilled in the art. Such gelling conditions can result in a gel time ranging from about 1 minute (or less) to about 10 hours or longer. As used herein, gel time generally refers to the time until no visible or macro-flow of the hydrogel-forming composition is evident following exposure to basic conditions.

The hydrogel-forming composition may be an aqueous solution or suspension comprising the hydrogel-forming components (e.g., a thiosulfonate polymer derivative). The hydrogel-forming components can also be suspended in nonaqueous fluid carriers, including, without limitation, hyaluronic acid, dextran sulfate, dextran, succinylated noncrosslinked collagen, methylated noncrosslinked collagen, glycogen, dimethylsulfoxide, glycerol, dextrose, maltose, triglycerides of fatty acids (such as corn oil, soybean oil, and sesame oil), and egg yolk phospholipid. Alternatively, the hydrogel-forming composition can comprise hydrogel-forming components that are in dry form such as coarse or fine powders. Dry formulations of the hydrogel-forming components can be optionally be shaped, or molded into a variety of forms, including tablets, capsules or sheets.

In one embodiment, the hydrogel-forming composition can be prepared as a mildly buffered solution or suspension at a pH and temperature that inhibits gel formation. Upon exposure to a basic environment, the composition undergoes a change in pH sufficient to permit crosslinking and hydrogel formation. In another embodiment, the hydrogel-forming composition can be in the form of a dry powder that is dissolved in a suitable buffer at a suitable concentration, temperature, and pH to initiate crosslinking and hydrogel formation. As recognized by one of ordinary skill in the art, such buffers include any known buffer in which the thiosulfonate polymer derivative is soluble and the desired pH is achievable, including but not limited to sodium phosphate, PBS buffer, and borate buffer.

In another embodiment, the hydrogel-forming composition can be an unbuffered or substantively unbuffered solution or suspension of thiosulfonate polymer derivatives at a concentration and pH that will substantially inhibit hydrogel formation. Hydrogel formation can then be initiated by the addition of an aliquot of pH-adjusting reagent at a desired temperature. In a preferred embodiment, a kit can be provided comprising (in addition to a gel-forming composition) a separate predetermined aliquot of a reagent, suspension or solid formulation ready for admixture with the hydrogel forming composition.

V. Biological Applications

The hydrogel compositions of this invention are useful in a variety of applications, and are particularly suited for biological applications, including drug delivery, tissue engineering, device coatings, and wound closure.

A. Delivery Vehicle

In one embodiment, as discussed above, hydrogel compositions of the invention can be employed to deliver agents such as active agents. Active agents can be noncovalently associated with the hydrogel compositions by exposing the hydrogel forming components to the active agent during gel formation, or by subsequently contacting a hydrogel with the active agent. Active agents can also be covalently incorporated into the hydrogel either through direct linkage to the hydrogel-forming components, or indirectly through a crosslinking agent. Direct and indirect linkages may be formed through, for example, interactions with one or more sulfhydryl groups of the gel, reactive groups on the water-soluble polymer, or at a terminus thereof. In a preferred embodiment, active agents are attached to the water-soluble polymer of the hydrogel-forming components by way of a hydrolytically or enzymatically unstable linkage.

Active agents can also be incorporated into the hydrogel-forming components and hydrogel compositions of the invention through a combination of covalent and noncovalent interactions. In one embodiment, hydrogel-forming components or hydrogel compositions formed therefrom may be covalently linked to a cyclodextrin molecule which provides a non-covalent host for the formation of host guest complexes, and permits the association of the biologically active moieties through a combination of covalent and noncovalent interactions. In such an embodiment, the cyclodextrin molecules may be covalently attached to the hydrogel composition through a disulfide linkage formed between the cyclodextrin and the hydrogel forming components.

The hydrogel of this invention may also be used to deliver a broad variety of diagnostic agents such as radiologically opaque compounds and dyes. The hydrogel compositions of the present invention can also be used to deliver living cells to a desired site of administration. The delivered cells may be used for a variety of purposes including the release hormones and growth factors or the formation of new tissue. In order to entrap the cells within a formed hydrogel, the cells can be suspended in a suitable medium and then mixed with the hydrogel-forming components. The hydrogel-forming components can be added in variety of ways including but not limited to addition as: a dry powder or as a reconstituted solution which has not yet gelled. Alternatively, the hydrogel-forming components can be prepared as a mildly buffered solution or suspension at a pH that inhibits gel formation, and the cells are prepared in a buffered medium sufficient to maintain the viability of the cells upon admixture with the hydrogel-forming components. Formation of the hydrogel at the pH of the resultant combined hydrogel-forming components and cell culture medium will result in the entrapping the cells within the hydrogel composition.

Regardless of the specific composition employed, when used as a delivery means, the hydrogel and hydrogel-forming compositions of this invention provide a depot for sustained release of the materials, such as active agents, associated with or entrapped within the hydrogel, such that they may be released with a simple kinetic profile. Alternatively, the hydrogel can be prepared such that they release materials with two or more kinetic profiles, which may be accomplished by a variety of means. One approach is to employ two or more different hydrogel-forming compositions or two or more different formed hydrogel, each providing a different rate of release. Another approach includes providing an initial loading dose entrapped within the hydrogel in addition to a dose covalently or ionically associated with the gel, such that the materials associated with the hydrogel will be released over a longer time period. Still another approach by which the release profile can be controlled is to vary the component from which one or more of the hydrogel employed is formed, such that the hydrogel is degraded at different rates. It is also possible to employ combinations of the above-mentioned approaches for providing controlling release.

The hydrogel and hydrogel-forming compositions of this invention can be delivered to a patient by a variety of means including but not limited to subdermally (subcutaneously), orally, intravenously, intraperitoneally, dermally (transdermal delivery), intradermally, intratumorily, intraocularly, intravicscerally, intraglandularly, intravaginally, intrastromally, intrasynovially intrasinus, intraventricullarly, intrathecally, intramuscularly, and intrarectally. The hydrogel compositions of the invention can also be applied to surgical sites (before, during, or after surgery, or a combination thereof). It will be understood that certain sites are selected to achieve systemic distribution of materials and others, such as intraocular, intrathecal and intratumor are selected for targeted (i.e., local) delivery of materials.

B. Tissue Engineering

The hydrogel compositions of the invention can also be used for tissue engineering purposes, such as the formation of scaffold materials and tissue augmentation. Examples of soft tissue augmentation include sphincter (e.g., urinary, anal, esophageal) augmentation and the treatment of rhytids and scars. Examples of hard tissue augmentation applications include the repair and/or replacement of bone and/or cartilaginous tissue. The hydrogel composition can also be formed as a scaffold that provides a defined surface area for tissue growth.

A general method for effecting augmentation of tissue involves injecting solutions or suspensions of hydrogel-forming components within the tissue in need of augmentation. The pH of the hydrogel forming components may be adjusted through use of appropriate physiologically compatible buffer solutions. Generally a small gauge needle can be employed to minimize tissue damage. Once delivered, the composition will form the hydrogel in situ. When the hydrogel-forming composition contains bioactive agents such as collagen, the collagen can be incorporated into the matrix by reacting with the hydrogel-forming components as discussed above. Groups present on the hydrogel-forming components may also interact with groups present in the patient's tissue (e.g., pendant thiol groups present on the patients tissues) resulting in the attachment of the formed hydrogel to the tissues.

C. Vascular Occlusion

Formed hydrogel compositions that have been molded into the form of a tube, string or coil, which have been subject to dehydration or lyophilization can be surgically implanted or delivered via catheter to a site of vascular damage or malformation. Hydrogel compositions that have been subject to dehydration or lyophilization compact in size and will rehydrate inside the vessel, swelling to their original shape. The hydrogel of this invention can thus be employed to reinforce damaged vessel tissue as occurs for example in an aneurysm, or for the purpose of treating vascular occlusion.

D. Bioadhesive Applications and Wound Closure

In one preferred embodiment of this invention, the compositions of the invention can be prepared such that they are particularly suitable for use as bioadhesives, for example, for use in surgery and for wound closure. Such compositions are suitable for forming an attachment between the surfaces of two tissues, or between a native tissue surface and a normative tissue surface or a surface of a synthetic implant.

Generally, the compositions containing hydrogel forming components are applied to the surfaces of the tissues to be joined either as a dry formulation such as a powder or a thin sheet, or as a solution of hydrogel-forming components that may be applied by injecting, spraying or brushing. The tissues are then joined and held in place until the hydrogel is formed in situ. As the gel forms, it may react with pendant reactive groups present on the tissue surface to form covalent bonds that aid in anchoring the faces of the tissue to be joined.

Hydrogel formation will generally be complete by one hour but can be complete in substantially less time, such as from about 5 to about 10 minutes. The time required for joining the tissue will be affected by a number of variables including the type and concentration of the hydrogel-forming components employed, the presence of additional components such as collagen. It is possible to reduce the time required for hydrogel formation by either increasing the concentration of the hydrogel-forming compositions or adjusting the pH. Application of hydrogel-forming compositions in dry form will result in slower hydrogel formation as the materials will require rehydration.

E. Implant Coatings

Another use of the hydrogel compositions of the invention is as a biocompatible coating material on a device intended for implantation into the body (referred herein as implants). Implants include, without limitation, artificial blood vessels, heart valves, artificial organs, bone prostheses, implantable lenticules, vascular grafts, stents, stent/graft combinations, and so on.

For coating implants, solutions containing hydrogel-forming components can be applied to the surface of the implant by any convenient means including, but not limited to, brushing, dipping or spraying. The implant can be applied to the target tissue prior to hydrogel formation or after hydrogel formation. As discussed above, the hydrogel-forming components may interact with reactive pendant groups on the surface of the surrounding tissue and the implant, which will aid in anchoring the implant in position.

While coating the surface of implants will generally aid in anchoring the implant, coating may also provide additional benefits such reduced thrombogenicity, which is an important consideration in applications such as artificial blood vessels and heart valves, vascular grafts, vascular stents, and stent/graft combinations. The hydrogel-forming compositions may also be used to coat implantable surgical membranes (e.g., monofilament polypropylene) or meshes (e.g., for use in hernia repair).

F. Ophthalmic Applications

Because of their optical clarity, the hydrogel compositions of the invention are particularly well suited for use in ophthalmic applications, including gel-based eye drops for delivering active agents.

G. Prevention of Tissue Adhesions

Another use of the hydrogel compositions of the invention is to coat tissues in order to prevent the formation of adhesions following surgery or injury to internal tissues or organs. It may also be desirable to incorporate proteins such as albumin, fibrin or fibrinogen into the hydrogel composition to promote cellular adhesion.

In a general method for coating tissues to prevent the formation of adhesions following surgery, a thin layer of the hydrogel-forming components is applied to the tissues before substantial crosslinking has occurred. Application of the hydrogel-forming components to the tissue site may be by extrusion, brushing, spraying (as described above), or by any other convenient means. Following application of the hydrogel-forming components to the surgical site, crosslinking is initiated and allowed to continue in situ prior to closure of the surgical incision. Once crosslinking has reached equilibrium, tissues which are brought into contact with the coated tissues will not stick to the coated tissues. At this point in time, the surgical site can be closed using conventional means (sutures, and so forth).

In general, compositions that exhibit a relatively short gel time (i.e., 5-15 minutes following exposure to a basic environment) are preferred for use in the prevention of surgical adhesions, so that the surgical site may be closed relatively soon after completion of the surgical procedure.

All articles, books, patents and other publications referenced herein are hereby incorporated by reference in their entireties.

EXAMPLES

The preparation of hydrogel-forming components and the formation of hydrogel compositions comprising these components may be accomplished by a variety of means including those outlined below. However, the embodiments exemplified below are in no way to be considered as limiting the scope of the invention.

Unless otherwise indicated, all PEG reagents are available from Nektar Therapeutics, Huntsville, Ala. All other reagents are available from commercial suppliers such as Aldrich, St. Louis, Mo.

Example 1

Synthesis Of 4-Arm PEG 10 kDa Methanethiosulfonate and Hydrogel Formation

A. Sodium Methanethiosulfonate

Sodium methane sulfinate (3.0 g) and sulfur (1.41 g) in methanol (180 ml) were refluxed under argon for 45 minutes. The mixture was cooled to room temperature, filtered, and the filtrate evaporated to dryness under reduced pressure to obtain the product (3.2 g). NMR (DMSO-d6): 2.97 ppm (s, $CH_3SO_2SNa$), peak at 1.82 ppm (s, $CH_3SO_2Na$) absent.

Schematically, the reaction can be represented as follows:

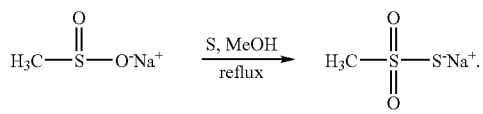

B. 4-Arm PEG 10 kDa Methanesulfonate 4-arm PEG 10 kDa, (MW 10,000; 20.0 g; 8 mmol of hydroxyl groups)(NOF Corporation, Tokyo, Japan/Nektar Therapeutics, Huntsville, Ala.) was dried by azeotropic distillation from 400 ml of chloroform. Chloroform (300 ml) was added to dissolve the residual syrup and the solution was cooled to 4° C. The flask was purged with dry argon and triethylamine ("TEA" 2.01 ml, 14.4 mmol) was injected followed by slow injection of methanesulfonyl chloride (1.02 ml, 13.2 mmol). The reaction mixture was stirred overnight under argon while the bath rose to ambient temperature. Anhydrous ethanol (5 ml) was added and the mixture stirred at room temperature for 30 minutes. Anhydrous sodium carbonate (10.0 g) was added to the reaction mixture and the resulting solution stirred at room temperature for one hour at which point it was filtered. The filtrate was concentrated to dryness, and 400 ml of 2-propanol was added. The precipitated product was collected by filtration and dried under vacuum. Yield: 20.0 g. NMR (DMSO-d$_6$): 3.51 ppm (s, PEG backbone), 4.31 ppm (t, —$CH_2OSO_2$—). Integration indicated 95.3% substitution by methanesulfonate.

Schematically, the reaction can be represented as follows:

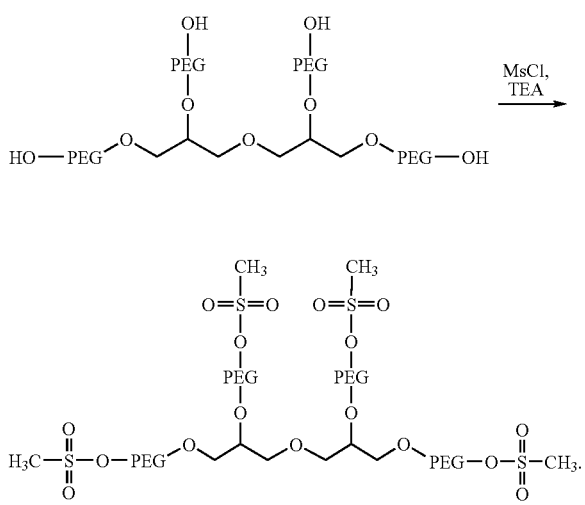

C. 4-Arm PEG 10 kDa-Methanethiosulfonate 4-arm PEG 10 kDa methanesulfonate (5.0 gm, 2.0 mmoles) was dried by azeotropic distillation. Anhydrous ethanol (80 ml) was added to the residual syrup. The flask was purged with dry argon. Sodium methanethiosulfonate (1.07 gm, 90%, 7.2 mmoles) was added under argon and the mixture refluxed under argon overnight. The mixture was filtered and the filtrate concentrated on a rotary evaporator at 40° C. until dry, followed by addition of 100 ml 2-propanol. The precipitated product was collected by filtration and dried under high vacuum overnight. The dried product (4.0 g) was dissolved in 100 ml of dichloromethane and washed with 100 ml of sodium phosphate buffer pH. 5.0 (10% w/v $NaH_2PO_4$—$Na_2HPO_4$). The aqueous solution was back extracted with three aliquots of dichloromethane (200 ml). The combined dichloromethane solutions were dried over anhydrous sodium sulfate. The mixture was filtered and the filtrate concentrated to near dryness on a rotary evaporator. The product was precipitated by the addition of 100 ml of 2-propanol and 100 ml ethyl ether. The precipitated product was collected by filtration and then dried under vacuum. Yield 3.1 g. NMR (DMSO-d$_6$):3.51 ppm (s, PEG backbone). The complete disappearance of peak at 4.31 ppm (t, —$CH_2OSO_2$—) indicated all mesylate groups had been substituted. The peak for the $CH_3SO_2S$— methyl group is under PEG backbone peak. Free sodium methanethiosulfonate was effectively removed based upon the absence of a peak at (2.94 ppm, s).

Schematically, the reaction can be represented as follows:

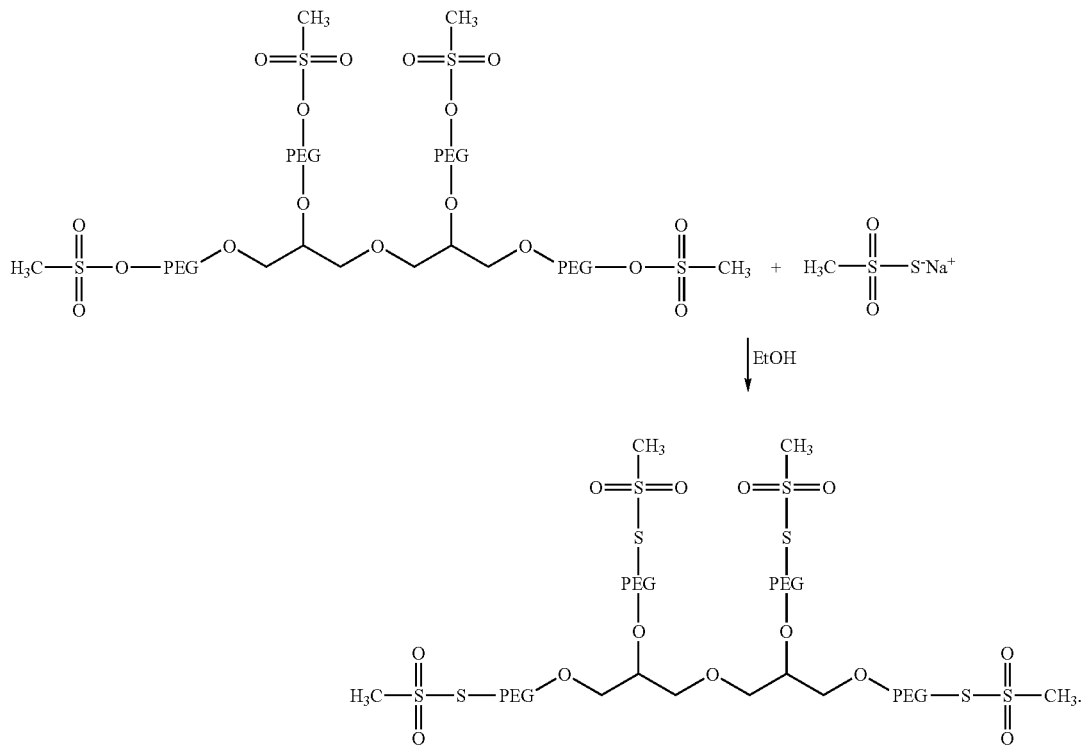

D. Hydrogel Formation From 4-Arm PEG 10 kDa-Methanethiosulfonate.

A 5% w/v solution of 4-arm PEG 10 kDa methanethiosulfonate was prepared in 100 mM sodium phosphate buffer (pH 8). The solution formed a hydrogel in about three hours at 23° C. and in about one hour at 37° C.

Schematically, the reaction can be represented as follows:

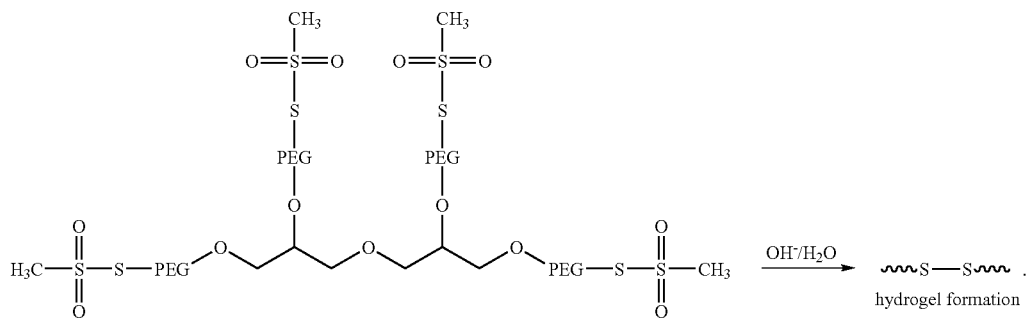

Example 2

Synthesis of 4-Arm PEG 10 kDa p-Toluenethiosulfonate and Hydrogel Formation

A. 4-Arm PEG 10 kDa Methanesulfonate 4-arm PEG 10 kDa, (20.0 g, 8 mmol of hydroxyl groups) (NOF Corporation, Tokyo, Japan) was dissolved in 400 ml of chloroform and evaporated to dryness under vacuum at 40° C. The residue was dissolved in 300 ml chloroform and the flask was purged with dry argon. Triethylamine ("TEA," 2.01 ml, 14.4 mmol) was added under argon. Methanesulfonyl chloride (1.02 ml, 13.2 mmol) was slowly added and the reaction mixture was stirred overnight under argon while the bath temperature rose to room temperature. Anhydrous ethanol (5 ml) was added and the mixture stirred at room temperature for 30 minutes. Sodium carbonate (10.0 g) was added and the solution was stirred at room temperature for one hour, after which the mixture was filtered. The filtrate was concentrated to dryness, followed by addition of 400 ml of 2-propanol. The precipitated product was collected by filtration and dried under vacuum. Yield 20.0 g. NMR (DMSO-d6):3.51 ppm (s, PEG backbone), 4.31 ppm (t, —$CH_2OSO_2$—). Integration indicated 95% substitution by methanesulfonate.

Schematically, the reaction can be represented as follows:

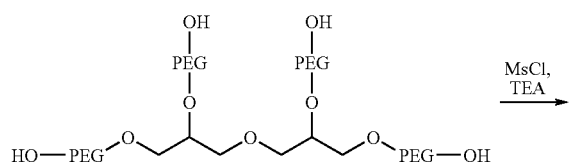

B. 4-Arm PEG 10 kDa p-Toluenethiosulfonate 4-arm PEG 10 kDa methanesulfonate, (10.0 gm, 4.0 mmoles) in chloroform (100 ml) was evaporated to dryness on rotary evaporator at 40° C. The flask was purged with dry argon and 150 ml of anhydrous ethanol was added to the remaining syrup followed by addition of 3.734 g (16.0 mmoles) of potassium p-toluenethiosulfonate. The mixture was refluxed under argon overnight and the solvent removed under vacuum. The product was dissolved in 500 ml of 1M $NaH_2PO_4$—$Na_2HPO_4$ buffer solution pH 5.8, containing 10 wt % NaCl, and the aqueous solution was extracted three times with 200 ml aliquots of dichloromethane. The combined dichloromethane extracts were dried over anhydrous sodium sulfate evaporated to dryness, and the product precipitated with 100 ml of 2-propanol and 100 ml of ethyl ether. The product was collected by filtration and dried under vacuum. Yield 8.1 g. NMR (DMSO-d6): 1.37 ppm (s, —$OC(CH_3)_3$), 2.43 ppm (s, $CH_3$—$CH_2$=$CH_2$/Ar), 3.51 ppm (s, PEG backbone), 6.76 ppm (t, —$CH_2NH$—CO—), 7.49 ppm (dd, $CH_3$—$CH_2$=$CH_2$/Ar), 7.82 ppm (dd, $CH_3$—$CH_2$=$CH_2$/Ar). Based upon integration, the product was 95% substituted.

Schematically, the reaction can be represented as follows:

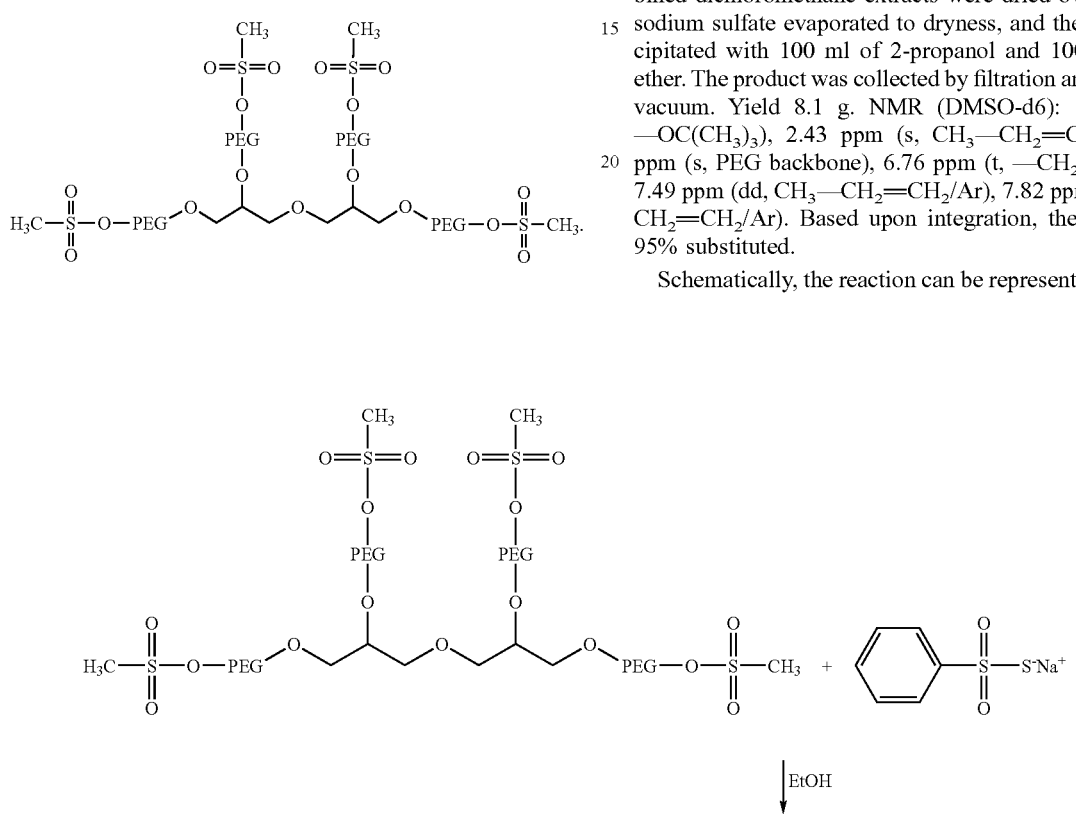

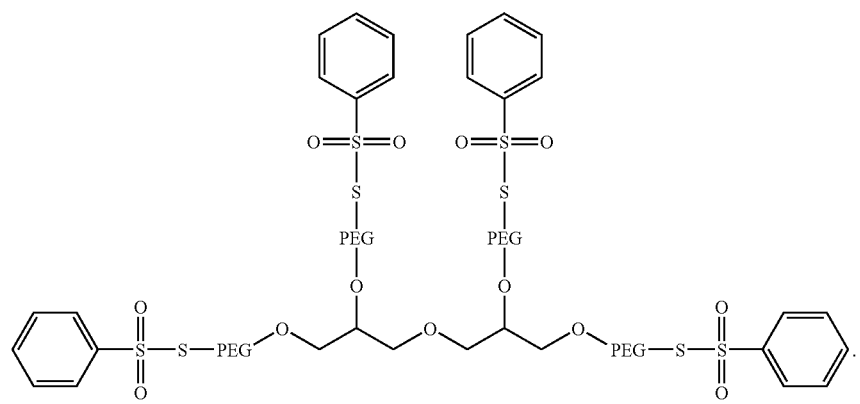

C. Hydrogel Formation

A 5% w/v solution of 4-arm PEG 10 kDa p-toluenethiosulfonate was prepared in 100 mM sodium phosphate buffer (pH 8). The solution formed a hydrogel in about three hours at 23° C. and in about one hour at 37° C.

Schematically, the reaction can be represented as follows:

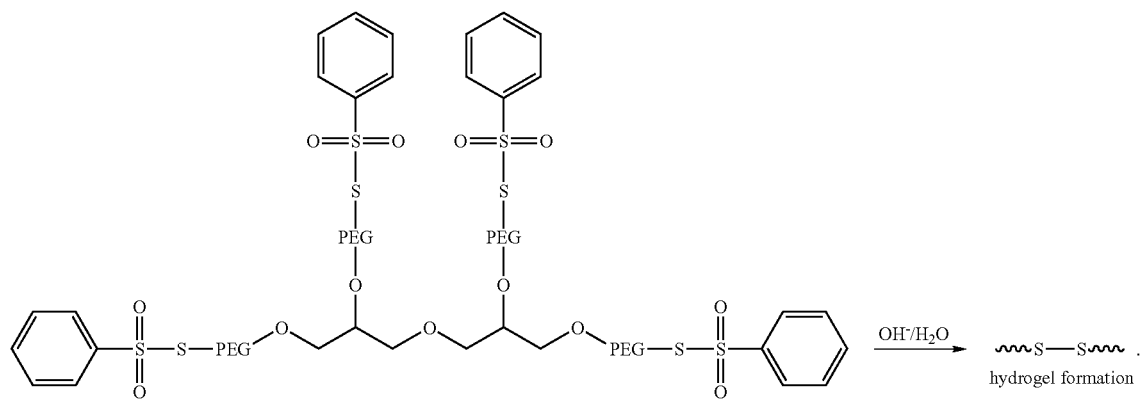

Example 3

Synthesis of 4-Arm PEG (2-Amidoethyl) Methanethiosulfonate and Hydrogel Formation A. Synthesis of 4-Arm PEG (2-Amidoethyl) Methanethiosulfonate 4-arm PEG 10 kDa 1-benzotriazolyl carbonate (4-arm PEG BTC) (4.0 g, 1.6 mmol of -BTC) available from Shearwater Corporation was dissolved in 40 ml of anhydrous acetonitrile. Tetraethyl ammonium acetate ("TEA," 0.67 ml, 4.8 mmol) was added, followed by addition of 2-(aminoethyl) methanethiosulfonate HBr salt (0.378 gm, 1.6 mmol., Toronto Research Chemicals). The reaction mixture was stirred at room temperature overnight and the solvent evaporated under vacuum. The product was precipitated by the addition of 2-propanol (100 ml) with vigorous stirring. The product was collected by filtration, rinsed with ether, and dried under vacuum. Yield: 3.7 g. NMR (DMSO-d6):4.07 ppm (t, —CH$_2$C(=O)N—), 3.51 ppm (s, PEG backbone), 7.54 ppm (—C(=O)NH—). Peak for the CH$_3$SO$_2$S— methyl group is under the PEG backbone peak. Based upon integration, the product was 99% substituted.

Schematically, the reaction can be represented as follows:

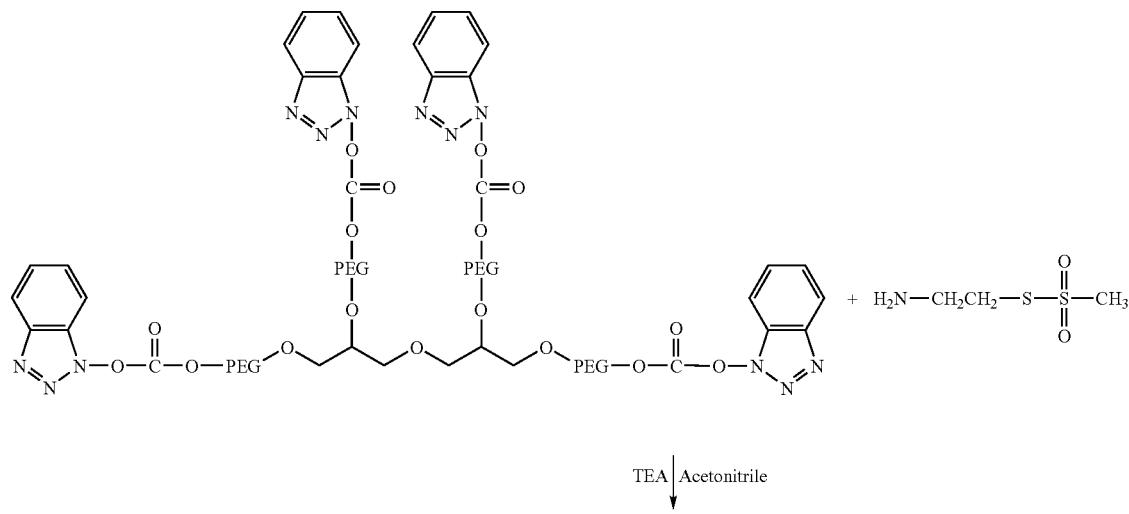

-continued

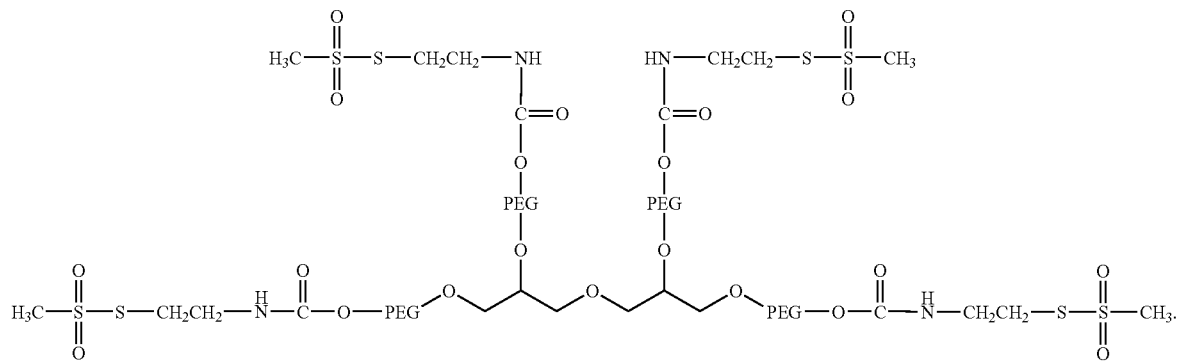

B. Hydrogel formation

A 5% w/v solution of 4-arm PEG (2-amidoethyl) methanethiosulfonate was prepared in 100 mM sodium phosphate buffer (pH 8). The solution formed a hydrogel in about three hours at 23° C. and in about one hour at 37° C.

Schematically, the reaction can be represented as follows:

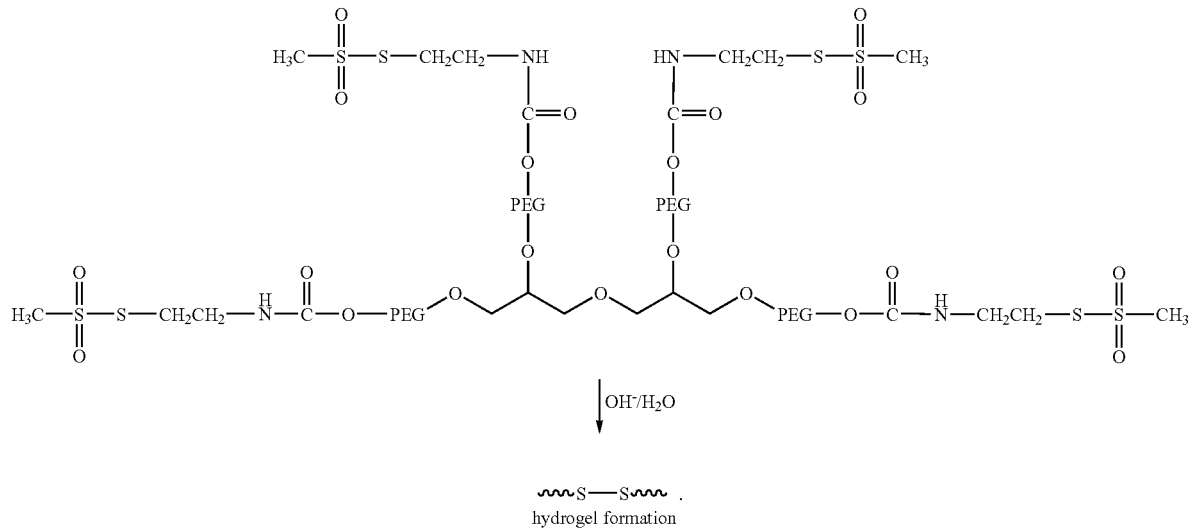

Example 4

Synthesis of 4-Arm PEG-Glutaryl-(2-Amidoethyl) Methanethiosulfonate and Hydrogel Formation A. Synthesis of 4-Arm PEG-glutaryl-(2-amidoethyl) Methanethiosulfonate To 1-benzotriazolyl 4-arm PEG glutarate (MW 10,000 DA, 5.0 g, MW 10 kDa, 2.0 mmol benzotriazolyl group, Nektar Therapeutics, Huntsville, Al) in anhydrous chloroform (60 ml) was added methyl 2-amino-1-ethanethiosulfonate (0.472 gm, 2.0 mmol) followed by triethylamine ("TEA," 0.84 ml, 6.0 mmole) and the mixture was stirred overnight. The solvent was removed by evaporation under vacuum and the product precipitated by addition of 2-propanol with vigorous stirring. The product was collected by filtration, washed with ethyl ether, and dried under vacuum.

Yield: 4.7 g. NMR (DMSO-d6):8.12 ppm (—C(═O)NH—), 4.12 ppm (t, —CH$_2$—O—C(═O)—), 3,51 ppm (s, PEG backbone), 2.31 ppm (t, —O—C(═O)CH$_2$—), 2.12 ppm (t, —CH$_2$C(═O)N—), 1.74 ppm (m, —(O═C)—C—CH$_2$—C—C(═O)—). 90% substitution was determined.

Schematically, the reaction can be represented as follows:

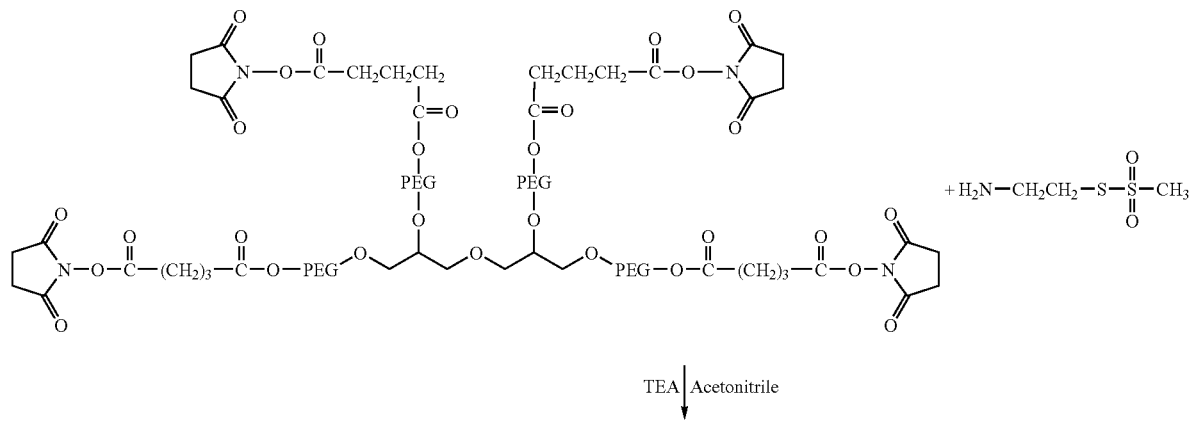

B. Hydrogel Formation

A 5% solution of 4-arm PEG-glutaryl-(2-amidoethyl) methanethiosulfonate was dissolved in 100 mM sodium phosphate buffer (pH 7.4). The solution formed a hydrogel in about 1 hour at 23° C.

Schematically, the reaction can be represented as follows:

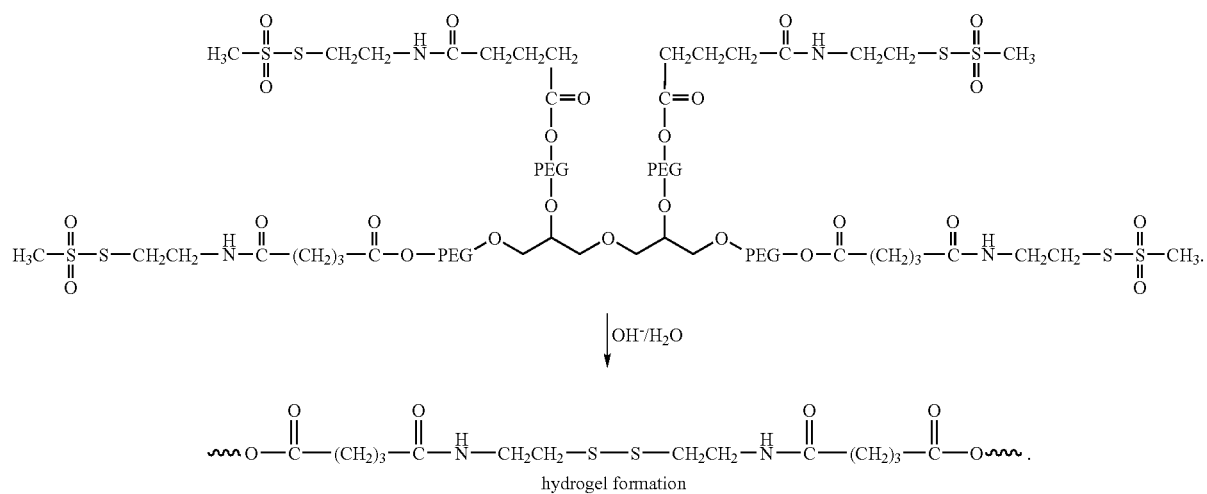

Example 5

Formation of Hydrogel From 4-Arm 10 kDa PEG Methanethiosulfonate and 4-Arm 10 kDa PEG Thiol A 5% wt./vol. solution (5 ml) of 4-arm 10 kDa PEG methanethiosulfonate in 0.1 M sodium phosphate buffer and a 5% wt./vol. solution (5 ml) of 4-arm 10 kDa PEG thiol were mixed with shaking at room temperature. A hydrogel formed in less than one minute.

Schematically, the reaction can be represented as follows:

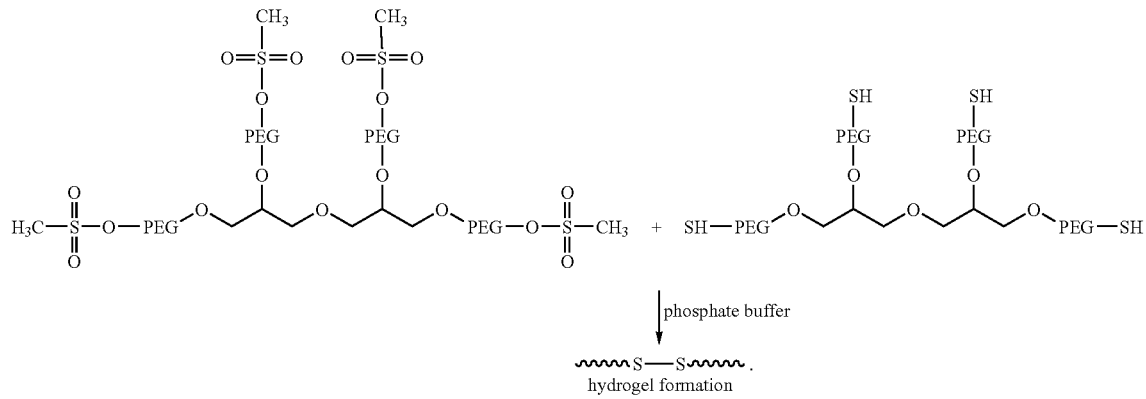

Example 6

Effects of Buffer pH, Temperature and Polymer Wt % On Gel Time

Several gelation conditions, including temperature, the weight percentage of components which will form the hydrogel (polymer weight concentration), pH of buffer solution, affect the rate of hydrogel formation. The effects of variables on gelation time were observed in the following experiments.

Sodium phosphate buffers (0.1 M pH at 7.00, 7.50, 8.00 respectively) were used to dissolve 4-arm PEG10 kDa-methanethiosulfonate (Nektar Therapeutics, Huntsville, Ala.) in the glass vials at the concentration (% wt/vol) listed in Table 1. Each vial contained 1000 mg mixtures of 4 arm PEG 10 kDa methanethiosulfonate and buffer. Each vial was shaken while dissolving and was then incubated without agitation at room temperature (24° C.) or in an incubator (37.0° C.) as recorded in the following table. Gel time was recorded for each vial. When the vial was turned upside down, the gel was considered formed if the material did not begin flowing immediately.

Results are detailed in Table 1, below.

TABLE 1

Effects of Polymer Concentration, Buffer Solution pH and Incubating Temperature on Gel Time

| Vial No. | Gel Time (min) | Conc. (% wt/vol) | 0.1M Sodium phosphate buffer pH | Incubating Temperature (° C.) |
|---|---|---|---|---|
| 1 | 585 | 2% | 7.50 | 24 |
| 2 | 259 | 2% | 8.00 | 24 |
| 3 | 205 | 2% | 7.50 | 37 |
| 4 | 81 | 2% | 8.00 | 37 |
| 5 | 682 | 5% | 7.00 | 24 |
| 6 | 230 | 5% | 7.50 | 24 |
| 7 | 103 | 5% | 8.00 | 24 |
| 8 | 175 | 5% | 7.00 | 37 |
| 9 | 70 | 5% | 7.50 | 37 |
| 10 | 40 | 5% | 8.00 | 37 |
| 11 | 586 | 10% | 7.00 | 24 |
| 12 | 210 | 10% | 7.50 | 24 |
| 13 | 103 | 10% | 8.00 | 24 |
| 14 | 155 | 10% | 7.00 | 37 |
| 15 | 65 | 10% | 7.50 | 37 |
| 16 | 35 | 10% | 8.00 | 37 |

Many modifications and other embodiments of the invention will come to mind to one skilled in the art to which this invention pertains having the benefit of teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for making a crosslinked polymer composition capable of forming a hydrogel comprising:
providing a first composition comprising at least one thiosulfonate polymer derivative, wherein said at least one thiosulfonate polymer derivative has the formula,

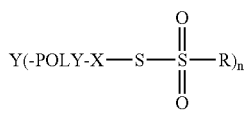

wherein POLY is a water-soluble polymer, (n) is 3 to about 25, X is a linking group, Y is a moiety derived from a molecule having at least three nucleophilic groups, and R is hydrogen, or an organic radical;
exposing said first composition to a base under conditions sufficient to initiate crosslinking between said thiosulfonate functional groups; and
allowing said crosslinking to proceed to thereby form said crosslinked polymer composition capable of forming a hydrogel.

2. The method of claim 1, wherein said first composition is substantially free of a crosslinking agent or redox catalyst.

3. The method of claim 1, wherein said at least one thiosulfonate polymer derivative is a 3 to about 100 arm thiosulfonate ester of a water-soluble polymer.

4. The method of claim 1, wherein said first composition comprises a single thiosulfonate polymer derivative component capable of crosslinking upon exposure to a base.

5. The method of claim 1, wherein POLY is a poly (ethyene glycol); (n) is 4; X is selected from the group consisting of alkylene groups, alkylene amides, alkylene esters, and alkylene ethers; and Y is derived from a moiety selected from the group consisting of glycerol, oligoglycerols, pentaerythritol, carbohydrates, cyclodextrin, and amine analogues thereof.

6. The method of claim 1, wherein said first composition further comprises at least one active agent.

7. The method of claim 6, further comprising incorporating at least one biologically active moiety in the hydrogel.

8. The method of claim 6, wherein said at least one biologically active moiety is entrapped within the crosslinked polymer composition during said crosslinking or is covalently linked to said at least one thiosulfonate polymer derivative.

9. A method for forming a crosslinked polymer composition capable of forming a hydrogel having desired physical properties from a single component hydrogel-forming composition, said method comprising:

providing a single component hydrogel-forming composition comprising a thiosulfonate polymer derivative, wherein said thiosulfonate polymer derivative has the formula,

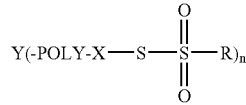

wherein POLY is a water-soluble polymer, (n) is 3 to about 25, X is a linking group, Y is a moiety derived from a molecule having at least three nucleophilic groups, and R is hydrogen, or an organic radical;

exposing said single component hydrogel forming composition to a base under conditions sufficient to initiate crosslinking between said thiosulfonate functional groups; and allowing said crosslinking to proceed and thereby form said crosslinked polymer composition capable of forming a hydrogel.

10. The method of claim 9, wherein said base has a pH ranging from about 7.4 to about 9.0.

11. The method of claim 9, wherein said single component hydrogel-forming composition is exposed to said base at a temperature ranging from about 20° C. to about 50° C.

12. The method of claim 9, wherein said thiosulfonate polymer derivative is present in said single component hydrogel-forming composition at a concentration ranging from about 2% w/v to about 25% w/v.

* * * * *